United States Patent [19]

Waller

[11] Patent Number: 5,233,077

[45] Date of Patent: Aug. 3, 1993

[54] PREPARATION OF N-VINYL-O-ALKYL CARBAMATE

[75] Inventor: Francis J. Waller, Allentown, Pa.

[73] Assignee: Air Products and Chemicals, Inc., Allentown, Pa.

[21] Appl. No.: 861,678

[22] Filed: Apr. 1, 1992

[51] Int. Cl.⁵ .......................................... C07C 261/00
[52] U.S. Cl. .................................................. 560/157
[58] Field of Search ......................................... 560/157

[56] References Cited

U.S. PATENT DOCUMENTS

| | | | |
|---|---|---|---|
| 2,592,254 | 4/1952 | Dickey | 260/77.5 |
| 3,019,231 | 1/1962 | Peppel et al. | 260/307 |
| 3,715,385 | 2/1973 | Wolgemuth et al. | 260/482 |
| 4,459,236 | 7/1984 | Merger et al. | 260/453 |
| 4,490,557 | 12/1984 | Dawson et al. | 564/159 |
| 4,572,804 | 2/1986 | Mullins | 260/453 |
| 4,574,159 | 3/1986 | Hassdenteufel | 560/157 |
| 4,701,549 | 10/1987 | Mullins | 560/159 |

OTHER PUBLICATIONS

Bull. Soc. Chem. Belg. 66 pp. 229–243 (1957).
J. Org. Chem. 10 pp. 483–497 (1945).

Primary Examiner—Michael L. Shippen
Attorney, Agent, or Firm—Keith D. Gourley; James C. Simmons; William F. Marsh

[57] ABSTRACT

N-vinyl-O-methyl carbamate is formed preferentially by heating dimethyl ethylidene dicarbamate in the liquid phase at a temperature of 155° to 350° C. and at a pressure which permits the vinyl carbamate to vaporize as it is formed. This vinyl carbamate is quickly condensed and can then be separated from the methyl carbamate which also emanates from the liquid phase. The yield of N-vinyl-O-methyl carbamate is enhanced by including carbon in the liquid phase in contact with the dimethyl ethylidene dicarbamate as it is pyrolyzed. Using carbon in the same manner is advantageous in producing other lower alkyl N-vinyl-O-alkyl carbamates. Preferably the carbon has a surface area of 300 to 1500 m²/g and is present in an amount such that the weight ratio of dialkyl ethylidene dicarbamate to carbon is in the range of 50 to 500. The product is a monomer which can be used in making amine-functional polymers.

16 Claims, No Drawings

PREPARATION OF N-VINYL-O-ALKYL CARBAMATE

CROSS-REFERENCE TO RELATED APPLICATIONS

This Application is related to copending Application Ser. No. 07/861,708, filed Apr. 1, 1992.

FIELD OF INVENTION

This invention relates to the preparation of N-vinyl-O-methyl carbamate by pyrolysis of dimethyl ethylidene dicarbamate (bis-carbamate). In another aspect it relates to the carbon catalyzed decomposition of dialkyl ethylidene dicarbamate to form N-vinyl-O-alkyl carbamate.

BACKGROUND OF INVENTION

The methyl ester of vinyl carbamic acid has been known for at least 40 years as a monomer which can be readily polymerized. Example 4 of U.S. Pat. No. 2,592,254, Dickey (1952) describes copolymerizing vinyl acetate and the methyl ester of vinyl carbamic acid to form a solid molding resin. The vinyl carbamic acid ester is said to have been prepared by reacting methyl urethane and acetylene. In general the patent discloses preparing amides or esters of unsaturated carbamic acids by heating urea or urethane with acetylene in the presence of a catalyst, such as a mixture of potassium hydroxide and zinc oxide. The process requires heating acetylene under pressure of at least 25 atmospheres using temperatures in the range of 150° to 250° C.

The polymerizability of N-vinyl-O-methyl carbamate is also disclosed by Bull. Soc. Chem. Belg. 66, pages 229–43 (1957) wherein it is stated that this monomer can be polymerized in solution in the presence of diazo-bis-isobutyronitrile. The synthesis of N-vinyl carbamates such as methyl and ethyl vinyl carbamates is by reaction of vinyl isocyanate with methyl or ethyl alcohol in the absence of a solvent. The melting point for N-vinyl-O-methyl carbamate which is soluble in methanol is given as 48°–9° C.

Another route to vinyl carbamates is disclosed by U.S. Pat. No. 3,019,231, Peppel, et al. (1962) which describes the vinylation of urethanes by reaction with vinyl ethers catalytically. The preferred catalyst is a mercuric salt of a mineral acid, e.g. mercuric sulfate. In Example III, N-methyl ethyl urethane was vinylated by reaction with methyl vinyl ether, producing N-vinyl-N-methyl ethyl urethane, useful as a comonomer in resin formation.

U.S. Pat. No. 3,715,385, Wolgemuth, et al. (1973) describes still another method of obtaining N-vinyl carbamic acid esters by condensation-re-arrangement of acrylonitrile carbonate with methanol or ethanol. In Example I, methyl (N-vinyl carbamate) was obtained in 40% yield from carboethoxy acrylohydroxamate at 100° C. using a sodium alkoxy tin catalyst. The carboethoxy acrylohydroxamate is said to decompose at reaction temperature to yield acrylonitrile carbonate.

More recently, U.S. Pat. No. 4,574,159, Hassdenteufel (1986) describes pyrolysis of N-α-methoxyethyl-O-methyl urethane to form N-vinyl-O-methyl urethane. Referring to the disclosure of Bull. Soc. Chem. Belg. (supra), it states that the process described therein cannot be readily practiced industrially because it relies upon thermal decomposition of explosive acryloyl azide. The method of the invention described in this patent obtains the pyrolysis starting material by electrochemical oxidation of N-ethyl-O-methyl urethane. The pyrolysis splits off methanol to form the vinyl group. Recovery of the N-vinyl-O-methyl urethane is by cooling the pyrolyzed mixture to 20° to −80° C., thereby crystallizing out an almost pure product. The mother liquor can be used in another pyrolysis.

Another use for N-(1-alkenyl)-carbamates is disclosed by U.S. Pat. No. 4,459,236, Merger, et al. (1984) which indicates that such alkenyl carbamates can be converted to 1-alkenyl isocyanates at elevated temperatures. The process begins by reacting an aldehyde with a carbamate to provide the N-(1-alkenyl)-carbamate which is then split at elevated temperature. Methyl carbamate is listed as a suitable starting material. Acetaldehyde, although not a preferred starting material, is also listed among many suitable aldehydes. These materials can be reacted at 10°–60° C. in a solvent and in the presence of 0.001 to 0.05 equivalents of an acid such as HCl. Pyrolysis to the 1-alkenyl isocyanate is carried out in the vapor or liquid phase at 250°–600° C. This process appears to proceed contrary to the results described many years earlier in J. Org. Chem. 10, pages 483–497 (1945) which discusses condensation of carbonyl compounds by interacting acetaldehyde with ethyl carbamate in the presence of hydrochloric acid to prepare diethyl ethylidene dicarbamate. This study included a series of saturated aliphatic carbamates, from ethyl carbamate and higher aliphatic esters, interacted with a group of aliphatic carbonyl derivatives. Condensation was found to take place in the ratio of 2 moles of carbamate to 1 mole of carbonyl compound to form dialiphatic bis-carbamates with a small amount of concentrated hydrochloric acid serving as a catalyst to initiate the exothermic reaction. The product was recovered by crystallization. Methyl carbamate was not included in this study.

U.S. Pat. No. 4,572,804, Mullins (1986) says that $\alpha,\beta$-unsaturated monoiso-cyanates are the pyrolysis product obtained on heating $\alpha,\beta$-saturated geminal bis-carbamates. Pyrolysis conditions include temperatures from 100° to 600° C. for 0.5 to 5 seconds. The geminal bis-carbamates are preferably made by reaction between a carbamate and an $\alpha, \beta$-unsaturated ether. In Example 2, vinyl isocyanate is made by pyrolysis of dimethyl ethylidene dicarbamate and distilling off the vinyl isocyanate. The undistilled material is said to be a mixture of carbamates including N-vinyl-O-methyl-carbamate.

U.S. Pat. No. 4,701,549, Mullins (1987) has the same disclosure, adding that this mixture which also contains methyl [(ethenylamino)carbonyl] carbamate can be polymerized to form a bonding resin. The pyrolysis of bis-compounds to form a polymerizable monomer is also described by U.S. Pat. No. 4,490,557, Dawson, et al. (1984) which discloses reaction of formamide and acetaldehyde in the presence of an acidic catalyst to form ethylidene bis formamide which can then be pyrolyzed to N-vinyl formamide, a monomer useful in preparing amine-functional polymers. Such polymers have attracted considerable interest because of their utility as flocculants and paper strength additives. The utility of N-vinyl formamide in this service stimulated my interest in the N-vinyl carbamates which can also be polymerized to a polymer hydrolyzable to contain amine functionality. Such a monomer offers an industrially attractive route to such polymers because urea and methanol can be easily reacted to form methyl carbonate which can then be reacted with acetaldehyde to form dimethyl ethylidene dicarbamate. An improved method for carrying out this latter process is the subject of my related co-pending application cross-referenced above. Pyrolysis of the bis-carbamate to vinyl carbamate rather than vinyl isocyanate presents a challenge which is addressed by the present invention.

SUMMARY OF THE INVENTION

I have found that N-vinyl-O-methyl carbamate can be formed in reasonably high yields by heating dimethyl ethylidene dicarbamate in a liquid phase to a temperature in the range of 155° to 350° C. and at a pressure which permits N-vinyl-O-methyl carbamate to vaporize from the liquid as it is formed. Vapor from the liquid is collected in a condensation zone and cooled, thereby condensing the vaporized N-vinyl-O-methyl carbamate along with methyl carbamate which also emanates from the liquid phase. The N-vinyl-O-methyl carbamate can then be recovered by separation from the carbamate. This result is quite surprising in view of the general teaching of the prior art that pyrolysis of bis-carbamates leads directly to vinyl isocyanates which distill overhead.

A further improvement on this invention is obtained by carrying out the heating of the dialkyl ethylidene dicarbamate in the presence of carbon which preferably has a surface area of 300 to 1500 square meters per gram. In this manner the yield of the N-vinyl-O-alkyl carbamate, wherein the alkyl group has 1 to 4 carbon atoms, can be significantly increased.

DETAILED DESCRIPTION OF THE INVENTION

Amine functional polymers can be formed by polymerization or copolymerization of N-vinyl-O-methyl carbamate followed by hydrolysis of the carbamate functionality to amine functionality. For example, the vinyl carbamate can be copolymerized with vinyl acetate, thereby forming polymers which have both amine and hydroxy functionality after hydrolysis. By the process of this invention, the N-vinyl-O-methyl carbamate is prepared by thermally cracking dimethyl ethylidene dicarbamate which in turn can be obtained by reaction of acetaldehyde with methyl carbamate using an acidic catalyst. Such a synthesis is described in my copending application cross-referenced above. Other methods of forming dimethyl ethylidene dicarbamate can be used, but the preferred process uses acetaldehyde and methyl carbamate which can be easily formed from urea and methanol.

The pyrolysis of the dimethyl ethylidene dicarbamate must be carried out in a particular manner to avoid obtaining vinyl isocyanate instead of the desired vinyl carbamate. To do this the dimethyl ethylidene dicarbamate is heated in a liquid phase, preferably in the absence of a solvent although high boiling solvents can be used. The pyrolysis temperature is between 155° to 350° C., preferably between 180° to 280° C. Pyrolysis is under reduced pressure so that N-vinyl-O-methyl carbamate is vaporized from the liquid as it is formed. Preferably the pressure under which the N-vinyl-O-methyl carbamate is vaporized is less than 100 mm/Hg.

The process can be carried out either continuously by flowing the liquid phase dimethyl ethylidene dicarbamate through a heated zone or by batch operation as illustrated by the Examples. The pyrolysis time is generally from about 0.2 to 60 minutes in the batch mode or 0.1 to 30 minutes under continuous process conditions. Inert gases, such a nitrogen, can be introduced to aid in the removal of the vaporized N-vinyl-O-methyl carbamate.

The vaporized material, referred to as pyrolysate, is passed from the cracking zone quickly to a condensation zone where it is cooled and condensed along with vaporized methyl carbamate. Methanol has also been found to be present in the pyrolysate, indicating that isocyanate has been formed in the liquid phase, but under these conditions is not carried over in the pyrolysate vapor. Methanol can, therefore, be added to the liquid phase in order to reduce the presence of vinyl isocyanate which may result from over-cracking the dimethyl ethylidene dicarbamate. The N-vinyl-O-methyl carbamate can be separated from the other materials in the pyrolysate by cooling, by distillation under reduced pressure or by column chromatography.

Increased yields of the N-vinyl-O-methyl carbamate can be obtained by using carbons as catalysts in the pyrolysis process. In addition to N-vinyl-O-methyl carbamate, the corresponding ethyl, propyl and butyl compounds can be formed using the carbon catalyst to obtain N-vinyl-O-alkyl carbamate from dialkyl ethylidene dicarbamate wherein the alkyl groups contain 1 to 4 carbon atoms. Isopropyl and isobutyl derivatives are included as are n-propyl and n-butyl compounds. The starting carbamates can be synthesized from the corresponding alcohols as methyl carbamate is formed from urea and methanol.

Carbons which can be used are, in general, those which are considered to be not well-defined crystalline materials, but are characteristically amorphous although ordered in their structure, such as charcoal, coke and carbon black. Charcoals are porous solids containing 25 to 99% carbon produced by heating carbonaceous materials such as cellulose, wood, peat, and coals of bituminous or lower rank in the absence of air. Chars and charcoals from cellulose or wood are soft and pliable, while those obtained from nutshells, for example coconut shells, and from coal are dense, hard carbons.

Activated carbon is a suitable catalyst. Such carbon has an extensive network of internal pores of near molecular dimensions and internal surfaces on the order of 1000 $m^2/g$. Carbons with extremely high surface area have, however, been found not to give the advantageous yields observed with the lower surface area carbons and preferred carbons have a surface area not higher than 1500 $m^2/g$. Preferably the surface area of the carbon used for catalysis in this pyrolysis is on the order of 300 to 1500 $m^2/g$ as measured by the B.E.T. method using nitrogen.

The variety of carbons which can be employed is quite broad and advantages can be taken of the differences in pore size distribution or the chemical/polar nature of the surfaces of the carbons which tend to influence their function. Such carbons are made from various raw materials by chemical or high temperature steam activation processes. Coconut shell charcoal (cocochar) is a raw material for activated carbon which performs very well. Such carbons have very small pore radii. Coal-based carbons, another raw material type which is suitable, contain relatively larger pores. Commercial carbon grades which can be used include Norit ROX 0.8 which is an acid-washed pelletized carbon grade with a particle diameter of approximately 0.8 mm. It is made by the conventional process of steam activation to produce a uniform product. Also suitable are the granular Darco grades of carbon which are acid-washed, high efficiency lignite-based activated carbons. Both Norit and Darco carbons are products of American Norit Co., Inc. Carbon molecular sieves (CMS) which are well known carbon forms are also suitable as catalysts. In general such carbon molecular sieves are designated according to their effective pore opening size which is on the order of 3 to 5 angstroms. A carbon which appears to be less suitable is a cococharm which has been activated at 800° C. in nitrogen and tends to be more graphitic or crystalline in nature.

The amount of carbon used in such that the weight ratio of the bis-carbamate to carbon is in the range of about 50 to 500. While relatively small amounts of carbon have been found to be effective, it appears that if too much carbon is present during the pyrolysis, the advantages of increased yield of the N-vinyl-O-alkyl carbamate are not realized.

The reason why N-vinyl-O-methyl-carbamate is formed in reasonably high yields rather than vinyl isocyanate as predicted from the prior art, is not completely understood. While not to be bound by theory, it is believed that the explanation lies in the relative reactivities and solubilities of N-vinyl-O-methyl carbamate and vinyl isocyanate in solution in liquid bis-carbamate. Any vinyl isocyanate which is formed during the pyrolysis of the bis-carbamate, as indicated by the presence of methanol, remains in solution in the bis-carbamate. Since the vinyl isocyanate is more reactive than the vinyl carbamate, it is believed to polymerize and remain in the liquid phase, rather than distilling overhead. This permits a separation of the vinyl carbamate from the liquid phase by vaporization. Rapid condensation and colling occur before the vinyl carbamate can take part in any further decomposition. The carbon is believed to assist in this mechanism, but the manner in which it works is not fully understood. Other inorganic materials which were added to determine if they would likewise have catalytic effects either produced a negative result or no benefit.

The following specific embodiments of my invention are presented to illustrate the invention and should not be construed to limit it unduly.

EXAMPLE 1

This example shows synthesis of N-vinyl-O-methyl carbamate by thermal cracking of bis-carbamate using the procedure of the invention. Dimethyl ethylidene dicarbamate (10.2 g, 0.0579 mol) with a melting point of 128°-130° C. was added to a 100 ml round bottom flask equipped with a thermometer which could extend into the liquified bis-carbamate, magnetic stirring bar, and a short path minimum hold-up distillation head with one receiving flask. The distillation head assembly was connected to a trap immersed in dry ice and a vacuum source. The receiving flask was cooled with wet ice. A prewarmed heating mantle was connected to the round bottom flask and the top of the flask and distillation head assembly was wrapped with insulating material. Vacuum was maintained at approximately 30 mm Hg. Pyrolysis products started to collect when the temperature within the heated zone reached 190°-200° C. Collection continued for approximately 20 minutes. The temperature within the heated zone reached approximately 260° C. The pyrolysate weighed 8.1 g while the pot residue was 2.0 g.

From the NMR integration of the pyrolysate, the product composition was N-vinyl-O-methyl carbamate (2.7 g, 0.027 mol), methyl carbamate (4.3 g, 0.057 mol) and methanol (1.1 g, 0.034 mol). From the charged bis-carbamate, 4.34 g of methyl carbamate and 5.8 g of N-vinyl-O-methyl carbamate was the ultimate yield possible. Under these reaction conditions, a 46.5% yield of N-vinyl-O-methyl carbamate was realized. The methyl carbamate yield was 100% and the mol balance on vinylic and methanol was 0.061 which was in very good agreement with the charged bis-carbamate.

The pyrolysate from an analogous batch thermal cracking had a composition by weight of 35% N-vinyl-O-methyl carbamate (0.7 g), 54% methyl carbamate (1.1 g) an 11% methanol (0.2 g). This pyrolysate when placed on a silica gel (130–270 mesh, dried at 80° C. under vacuum for 3 hrs) column and eluted with methyl tert-butyl ether gave the results shown in Table 1. The total weight collected from the column was 1.8 g. When 0.2 g methanol is added to the collected weight (1.8 g) of N-vinyl-O-methyl carbamate and methyl carbamate, the final weight is the initial weight put on the column. The collected N-vinyl-O-methyl carbamate (0.6 g) had a melting point of 46° C. and was approximately the estimation from the spectroscopic analysis.

The N-vinyl-O-methyl carbamate product had the following spectroscopic characteristics:

$^1$HNMR ($\delta$, CDCl$_3$): 7.40 (br, 1H), 6.75 (m, 1H), 4.60 (d, 1H), 4.25 (d, 1H), 3.85 (s, 3H).

UV (dry methanol)$\lambda_{max}$ (1 g $\epsilon$) [nm]: 215 (4.3), 260 (3.0).

IR (KBr) [cm$^{-1}$]: 3300, 1715, 1645, 1255.

TABLE 1

Chromatographic Separation of $CH_2=CHNHCO_2CH_3/H_2NCO_2CH_3$

| Fraction (ml) | Wt. (g) | Total Wt. (g) | NMR Analysis |
| --- | --- | --- | --- |
| 60 | 0.02 | 0.02 | $CH_2=CHNCO_2CH_3$ |
| 10 | 0.013 | 0.033 | " |
| 5 | 0.155 | 0.188 | " |
| 5 | 0.173 | 0.361 | " |
| 5 | 0.124 | 0.485 | " |
| 5 | 0.106 | 0.591 | " |
| 5 | 0.056 | 0.657 | Mixture |
| 5 | 0.152 | 0.809 | $H_2NCO_2CH_3$ |
| 10 | 0.376 | 1.185 | " |
| 20 | 0.370 | 1.555 | " |
| 20 | 0.134 | 1.689 | " |
| 40 | 0.108 | 1.797 | " |

The above data of Table 1, in addition to helping to identify the products, show that the vinylic carbamate product and methyl carbamate can be separated chromatographically.

EXAMPLE 2

This example shows synthesis of N-vinyl-O-methyl carbamate by catalytic cracking of bis-carbamate in the presence of carbon. Dimethyl ethylidene dicarbamate (10 g, 0.057 mol) and 0.03 g coconut char (N$_2$ surface area 700–800 m$^2$/g) were heated in a similar fashion as Example 1. The pyrolysate weighed 8.7 g and the pot residue was 1.1 g. From the NMR integration of the pyrolysate, the product composition was N-vinyl-O-methyl carbamate (3.56 g, 0.035 mol), methyl carbamate (4.46 g, 0.059 mol) and methanol (0.67 g, 0.021 mol). Under these conditions, a 62.1% yield of N-vinyl-O-methyl carbamate was realized. The total mass recovered was 9.8 g.

EXAMPLES 3-15

The procedure in Example 1 was followed except types of carbon, amounts of carbon and pretreatment of carbons were varied. Pertinent yield data are given in Table 2.

TABLE 2

Cracking in the Presence of Carbon

| Example | Carbon Type | Carbon Surface Area ($m^2/g$) | Carbon Amount (g) | Bis-Carbamate (g) | Pyrolysate (g) | % Vinylic in Pyrolysate by NMR | % Yield Vinylic |
|---|---|---|---|---|---|---|---|
| 3 | Peat Based[1] | 900 | 0.03 | 9.98 | 8.2 | 42.5 | 60.7 |
| 4 | 3A CMS | N.D. | 0.03 | 10.0 | 8.3 | 39.2 | 56.7 |
| 5 | 5A CMS | N.D. | 0.03 | 10.0 | 7.9 | 42.4 | 58.4 |
| 6 | Granular DARCO[2] | 600 | 0.03 | 10.0 | 8.3 | 40.6 | 58.4 |
| 7 | Granular DARCO[2] | 600 | 0.1 | 9.99 | 8.2 | 45.5 | 65.0 |
| 8 | Anderson[3] | about 2700 | 0.03 | 9.99 | 7.9 | 30.3 | 41.7 |
| 9 | Fisher[4] | N.D. | 0.03 | 10.0 | 7.7 | 30.9 | 41.5 |
| 10 | Cocochar[5] | N.D. | 0.03 | 10.0 | 7.8 | 33.3 | 45.3 |
| 11 | Cocochar[6] | 700-800 | 0.03 | 10.0 | 8.1 | 37.5 | 52.9 |
| 12 | Cocochar[6] | 700-800 | 0.1 | 10.0 | 8.4 | 34.4 | 50.3 |
| 13 | Cocochar[6] | 700-800 | 0.3 | 10.1 | 7.1 | 31.9 | 39.5 |
| 14 | Cocochar[7] | 1100-1200 | 0.03 | 9.9 | 7.9 | 40.0 | 55.1 |
| 15 | Peat Based[1][6] | 900 | 0.03 | 10.0 | 7.9 | 39.6 | 54.5 |

[1]NORIT ROX 0.8 extruded pellet of American Norit Co., Inc.
[2]Lignite based, activated, 4-12 mesh carbon of Am. Norit.
[3]Obtained from Anderson Development Co.
[4]Activated carbon, 50 to 200 mesh of Fisher Scientific.
[5]Treated at 800° C. with $N_2$.
[6]Treated with nitric acid by stirring 20 g of carbon with 200 g of 10% $HNO_3$ by weight at room temperature for 2 hours. The carbon was filtered, washed with distilled water until the washings were neutral and dried in a vacuum oven under $N_2$ at 100° C. for 16 hours.
[7]8-16 mesh.

From the data of Table 2, Examples 3-7, 11, 12, 14 and 15 show vinylic yield improvement over thermal pyrolysis without carbon (Example 1: 46.5% yield.) The surface area of the carbon used in Example 8 was too high while that used in Example 9 is believed to have been too low. The cocochar of Example 10 is believed to have been too graphitic. The amount of carbon charged in Example 13 was too high in proportion to the bis-carbamate.

EXAMPLES 16-20

The following Examples compare carbon with other materials as a catalyst in the conversion of bis-carbamate to N-vinyl-O-methyl carbamate. The procedure followed in each case was as described in Example 1 except for the material added for possible catalytic effect as identified in Table 3 which also presents relevant data including yield of the desired vinylic carbamate.

TABLE 3

| Example | Added Material Type | (g) | Bis-Carbamate (g) | Pyrolysate (g) | % Vinylic in Pyrolysate | % Vinylic Yield |
|---|---|---|---|---|---|---|
| 16 | Acid Resin[1] | 1.0 | 10 | 6.7 | None | — |
| 17 | $Na_2CO_3$ | 0.3 | 10 | 7.4 | 33.3 | 43 |
| 18 | MgO | 0.3 | 10 | 7.4 | 30.4 | 39 |
| 19 | Quartz Chips[2] | | 10 | 7.1 | 25.8 | 32 |
| 20 | Cocochar | 0.03 | 10 | 8.5 | 37.5 | 56 |

[1]NR50 strong acid resin
[2]Same volume as the carbon of Example 20.

In the above Examples 16-20, only the carbon addition provided an improved yield over thermal cracking without added material as illustrated by Example 1 (46.5% yield).

Other advantages and embodiments of our invention will be apparent to those skilled in the art from the foregoing disclosure without departing from the spirit or scope of my invention.

I claim:

1. A process for making N-vinyl-O-methyl carbamate which comprises heating in a liquid phase dimethylethylidene carbamate in the presence of solid carbon particles to a temperature of 155° to 350° C. and at a pressure which permits N-vinyl-O-methyl carbamate to vaporize into a condensation zone as it is formed, cooling and condensing vaporized N-vinyl-O-methyl carbamate and methyl carbamate emanating from said liquid phase, and recovering said N-vinyl-O-methyl carbamate.

2. The process of claim 1 wherein said temperature is 180° to 280° C.

3. The process of claim 1 wherein said liquid phase is maintained without a separate solvent.

4. The process of claim 1 wherein a pressure of less than 100 mm Hg is maintained in said condensation zone.

5. A process for making N-vinyl-O-alkyl carbamate which comprises heating a liquid phase of dialkyl ethylidene dicarbamate, wherein each alkyl group contains 1 to 4 carbon atoms, to pyrolysis temperature in the presence of carbon having a surface area of 300 to 1500 square meters per gram, thereby vaporizing N-vinyl-O-alkyl carbamate from said liquid phase, and condensing said vaporized N-vinyl-O-alkyl carbamate.

6. The process of claim 5 wherein the weight ratio of dialkyl ethylidene dicarbamate to carbon is in the range of 50 to 500.

7. The process of claim 5 wherein said pyrolysis temperature is in the range of 155° to 350° C.

8. The process of claim 7 wherein the pressure on said liquid phase is less than 100 mm Hg.

9. The process of claim 5 wherein said carbon is granular, activated lignite-based carbon.

10. The process of claim 5 wherein said carbon is 3 to 5 angstrom carbon molecular sieve.

11. The process of claim 5 wherein said alkyl groups are methyl groups.

12. The process of claim 5 wherein said alkyl groups are ethyl groups.

13. The process of claim 5 wherein said alkyl groups are n-butyl groups.

14. A process for making N-vinyl-O-methyl carbamate which comprises heating in a liquid phase dimethylethylidene carbamate and methanol to a temperature of 155° to 350° C. and at a pressure which permits N-vinyl-O-methyl carbamate to vaporize into a condensation zone as it is formed, cooling and condensing vaporized N-vinyl-O-methyl carbamate and methyl carbamate emanating from said liquid phase, and recovering said N-vinyl-O-methyl carbamate.

15. The process of claim 14 wherein said temperature is 180° to 280° C.

16. The process of claim 14 wherein a pressure of less than 100 mm Hg is maintained in said condensation zone.

* * * * *